US00RE49373E

(19) United States
(12) Reissued Patent
Xu

(10) Patent Number: US RE49,373 E
(45) Date of Reissued Patent: Jan. 17, 2023

(54) SYSTEM AND METHOD FOR ADJUSTING CYTOMETER MEASUREMENTS

(71) Applicant: Becton, Dickinson and Company, Franklin Lakes, NJ (US)

(72) Inventor: Heng Xu, Castro Valley, CA (US)

(73) Assignee: Becton, Dickinson and Company, Franklin Lakes, NJ (US)

(21) Appl. No.: 16/431,590

(22) Filed: Jun. 4, 2019

Related U.S. Patent Documents

Reissue of:

(64) Patent No.: 10,145,793
Issued: Dec. 4, 2018
Appl. No.: 15/210,727
Filed: Jul. 14, 2016

U.S. Applications:

(60) Provisional application No. 62/192,997, filed on Jul. 15, 2015.

(51) Int. Cl.
*G01N 21/64* (2006.01)
*G01N 15/14* (2006.01)

(52) U.S. Cl.
CPC ..... *G01N 21/6428* (2013.01); *G01N 15/1429* (2013.01); *G01N 15/1459* (2013.01); (Continued)

(58) Field of Classification Search
CPC ..... G01N 15/1459; G01N 15/1429; G01N 21/6428; G01N 2015/1477; G01N 2021/6439
See application file for complete search history.

(56) References Cited

U.S. PATENT DOCUMENTS 4,704,891 A * 11/1987 Recktenwald ..... G01N 15/1012 250/252.1
4,777,133 A * 10/1988 Picciolo ..... C12Q 1/04 250/252.1

(Continued)

FOREIGN PATENT DOCUMENTS

EP 1431745 6/2004
EP 1431745 A1 6/2004

(Continued)

OTHER PUBLICATIONS

Internation Search Report and Written Opinion in International Application No. PCT/US2016/042207, dated Oct. 19, 2016.

*Primary Examiner* — Christina Y. Leung
*Assistant Examiner* — Deandra M Hughes
(74) *Attorney, Agent, or Firm* — Khin K. Chin; Bret E. Field; Bozicevic, Field & Francis, LLP

(57) ABSTRACT

Methods and systems for operating a flow cytometer can include forward scatter values, side scatter values, and fluorescence intensity values for events of an unstained sample and associating the fluorescence intensity values with forward scatter-side scatter side scatter plot regions. Methods and systems for operating a flow cytometer can also include measuring forward scatter values, side scatter values, and fluorescence intensity values for events of a stained sample, determining forward scatter-side scatter plot locations for the events of the stained sample, and for each event of the stained sample, subtracting the fluorescence intensity value associated with the forward scatter-side scatter plot region that contains the forward scatter-side scatter plot location of the stained sample event from the measured fluorescence intensity value of the stained sample event at that forward scatter-side scatter plot location.

17 Claims, 9 Drawing Sheets

(52) U.S. Cl.
CPC ..... *G01N 2015/1477* (2013.01); *G01N 2021/6439* (2013.01)

(56) References Cited

U.S. PATENT DOCUMENTS

| | | | | | |
|---|---|---|---|---|---|
| 4,857,451 | A * | 8/1989 | Schwartz | G01N 15/1012 | 435/7.24 |
| 5,093,234 | A * | 3/1992 | Schwartz | G01N 15/1012 | 356/213 |
| 5,599,932 | A * | 2/1997 | Bieniarz | C07D 219/14 | 544/361 |
| 5,658,751 | A * | 8/1997 | Yue | C07D 215/18 | 435/29 |
| 5,784,162 | A * | 7/1998 | Cabib | C12Q 1/6841 | 250/461.2 |
| 2004/0119974 | A1* | 6/2004 | Bishop | G01N 15/1459 | 356/317 |
| 2009/0203538 | A1* | 8/2009 | Sugioka | C07K 16/2803 | 506/18 |
| 2011/0282870 | A1* | 11/2011 | Herzenberg | G01N 15/1429 | 707/723 |
| 2013/0323825 | A1* | 12/2013 | Sekino | G01N 21/6486 | 435/287.2 |
| 2014/0309782 | A1* | 10/2014 | Sharpe | G05D 21/02 | 700/266 |
| 2015/0140577 | A1* | 5/2015 | Li | G01N 15/1459 | 435/7.24 |

FOREIGN PATENT DOCUMENTS

| | | | |
|---|---|---|---|
| JP | 2003083894 | A | 3/2003 |
| JP | 2010156679 | A | 7/2010 |

* cited by examiner

SYSTEM AND METHOD FOR ADJUSTING CYTOMETER MEASUREMENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims priority to U.S. Provisional Patent Application Ser. No. 62/192,997 filed on Jul. 15, 2015 and entitled "System and Method for Adjusting Cytometer Measurements", the content of which is hereby incorporated by reference in its entirety.

BACKGROUND OF THE INVENTION

Field of the Invention

This disclosure relates generally to the field of flow cytometry, and more particularly to methods for reducing error in sample analysis.

Description of the Related Art

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed through a detection region in which the particles are exposed to an excitation light, typically from one or more lasers, and the light scattering and fluorescence properties of the particles are measured. Markers, such as cell surface protein components of cells the presence of which can serve as a distinguishing characteristic, may be recognized by reagents that include fluorescent dyes to facilitate detection, identification, and characterization. Each reagent can include a label, typically a fluorescent molecule or "dye," conjugated to a detector molecule that will selectively attach to a particular marker, for example, a monoclonal antibody. A multiplicity of different particles or components may be distinguished by using spectrally distinct fluorescent dyes to label the markers. In some implementations, a multiplicity of photodetectors are included in the analyzer. When a particle passes through the laser beam, time correlated pulses on forward scatter (FSC) and side scatter (SSC) detectors, and possibly also fluorescent emission detectors will occur. This is an "event," and for each event the magnitude of the detector output for each detector, FSC, SSC and fluorescent emission detectors is stored. The data obtained comprise the signals measured for each of the light scatter parameters and the fluorescence emissions.

Cytometers may further comprise components for storing the detector outputs and analyzing the data. For example, data storage and analysis may be carried out using a computer connected to the detection electronics. For example, the data can be stored logically in tabular form, where each row corresponds to data for one particle (or one event), and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include FSC, which refers to the excitation light that is scattered by the particle along a generally forward direction, SSC, which refers to the excitation light that is scattered by the particle in a generally sideways direction, and the light emitted from fluorescent molecules in one or more channels (frequency bands) of the spectrum, referred to as FL1, FL2, etc., or by the name of the fluorescent dye that emits primarily in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

SUMMARY

In accordance with one aspect of the present invention, methods are provided for flow cytometry experiments.

In one embodiment, a method for operating a flow cytometer having a forward scatter detector, a side scatter detector, and a plurality of fluorescent emission detectors, each fluorescent emission detector corresponding to a fluorescence channel is provided. The method includes measuring one or more forward scatter values at the forward scatter detector, one or more side scatter values at the side scatter detector, and one or more fluorescence intensity values at one or more of the plurality of fluorescent emission detectors for one or more events of an unstained sample using the flow cytometer. The method further includes associating one or more fluorescence intensity values for one of more of the plurality of fluorescent emission detectors with one or more forward scatter-side scatter plot regions based at least in part on the measuring the one or more events of the unstained sample. The method further includes measuring one or more forward scatter values, one or more side scatter values, and one or more fluorescence intensity values at one or more of the plurality of fluorescent emission detectors for one or more events of a stained sample using the flow cytometer. The method further includes determining forward scatter-side scatter plot locations for the one or more events of the stained sample. The method further includes, for each of the one or more events of the stained sample, subtracting a fluorescence intensity value associated with the forward scatter-side scatter plot region that contains the forward scatter-side scatter plot location of the stained sample event for at least one of the plurality of fluorescent emission detectors from a measured fluorescence intensity value of the stained sample event at that forward scatter-side scatter plot location measured at the at least one of the plurality of fluorescent emission detectors.

In another embodiment, a flow cytometer is provided. The flow cytometer includes an excitation laser, a fluidics system configured to transport particles from one or more samples into a beam path of the excitation laser, one or more detectors, and a processing circuit. The one or more detectors are configured to measure one or more forward scatter values, one or more side scatter values, and one or more fluorescence intensity values for one or more events of an unstained sample and measure one or more forward scatter values, one or more side scatter values, and one or more fluorescence intensity values for one or more events of a stained sample. The processing circuit is configured to associate one or more fluorescence intensity values with one or more forward scatter-side scatter plot regions based at least in part on measurements of the one or more forward scatter values, one or more side scatter values, and one or more fluorescence intensity values for the one or more events of the unstained sample. The processing circuit is also configured to determine forward scatter-side scatter plot locations for the stained sample. The processing circuit is further configured to, for each of the one or more events of the stained sample, subtract a fluorescence intensity value associated with the forward scatter-side scatter plot region that contains the forward scatter-side scatter plot location of the stained sample event from a measured fluorescence intensity value of the stained sample event at that forward scatter-side scatter plot location.

BRIEF DESCRIPTION OF THE DRAWINGS

[The patent or application file contains at least one drawing executed in color. Copies of this patent or patent application publication with color drawing(s) will be provided by the Office upon request and payment of the necessary fee.]

DETAILED DESCRIPTION

The present invention provides systems and methods for performing flow cytometry experiments. Over the past several years, increases in the number of measurements made for the events of a flow cytometry experiment have been desired, and instrument manufacturers have developed flow cytometer instruments with detection systems and data analysis capabilities of increased complexity and performance. Advances in biochemistry have produced an increasingly large selection of fluorescent labels. Although these advances have made flow cytometry more useful than ever, harnessing that usefulness can still be a challenge. Label selection and instrument configuration are more complex, while at the same time experimental success is more dependent on appropriate experimental design. For example, the choice of fluorescent dyes used in a cytometry experiment is significant for the accuracy of the conclusions drawn from the data measured because the emission spectra from one fluorescent dye may overlap the detection bands of multiple detectors. Differences in relative brightness between labels and differences in the relative density of the markers labeled in an experiment can also affect the accuracy of event characterization.

Figure 1:
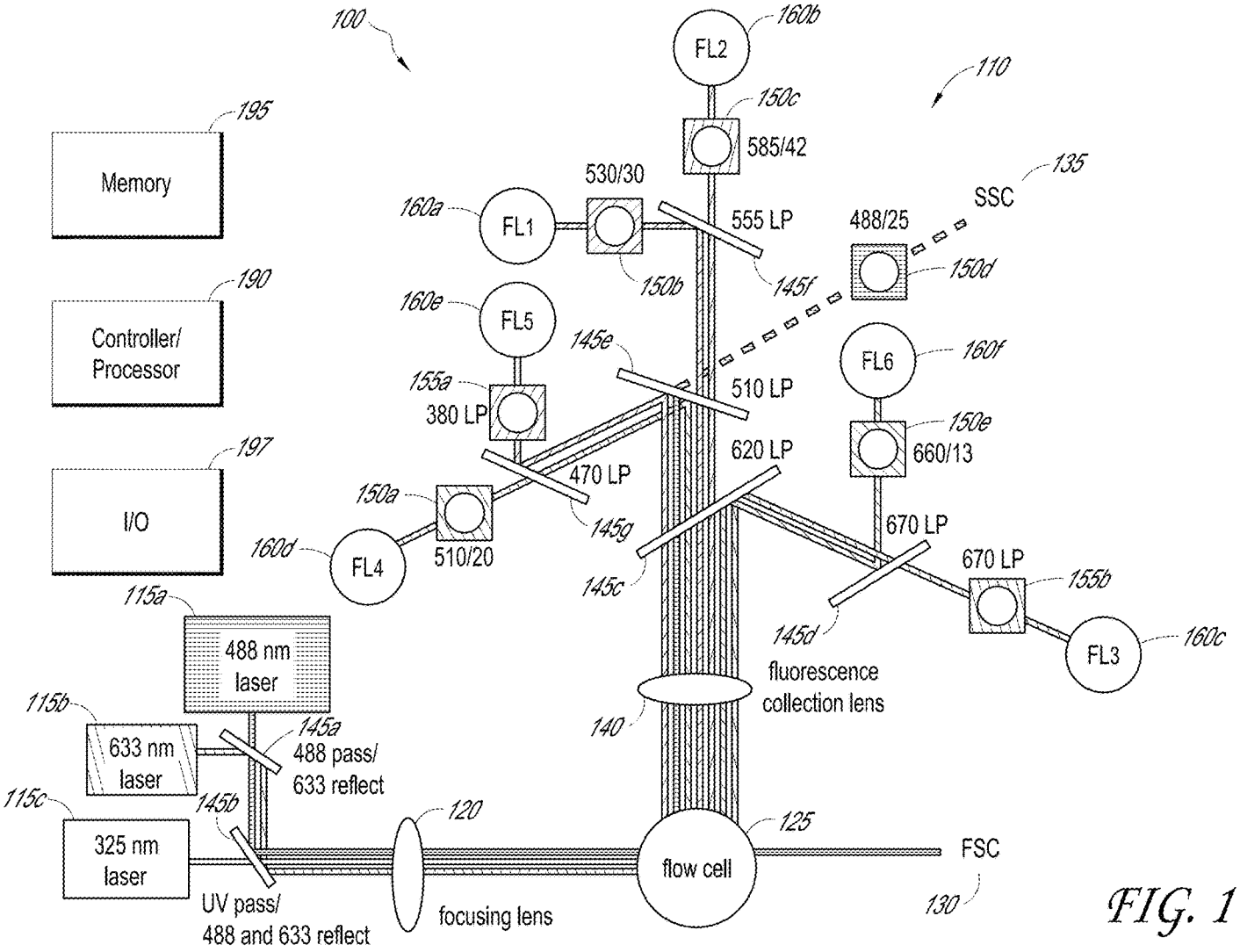
FIG. 1 depicts a flow cytometer in accordance with an illustrative embodiment of the present invention.

FIG. 1 shows a system 100 for flow cytometry in accordance with an illustrative embodiment of the present invention. The system 100 includes a flow cytometer 110, a controller/processor 190 and a memory 195. The flow cytometer 110 includes one or more excitation lasers 115a-c, a focusing lens 120, a flow chamber 125, a forward scatter detector 130, a side scatter detector 135, a fluorescence collection lens 140, one or more beam splitters 145a-g, one or more bandpass filters 150a-e, one or more longpass ("LP") filters 155a-b, and one or more fluorescent emission detectors 160a-f.

The excitation lasers 115a-c emit light in the form of a laser beam. The wavelengths of the laser beams emitted from excitation lasers 115a-c are 488 nm, 633 nm, and 325 nm, respectively, in the example system of FIG. 1. The laser beams are first directed through one or more of beam splitters 145a and 145b. Beam splitter 145a transmits light at 488 nm and reflects light at 633 nm. Beam splitter 145b transmits UV light (light with a wavelength in the range of 10 to 400 nm) and reflects light at 488 nm and 633 nm.

The laser beams are then directed to a focusing lens 120, which focuses the beams onto the portion of a fluid stream where particles of a sample are located, within the flow chamber 125. The flow chamber is part of a fluidics system which directs particles, typically one at a time, in a stream to the focused laser beam for interrogation. The flow chamber can comprise a flow cell in a benchtop cytometer or a nozzle tip in a stream-in-air cytometer.

The light from the laser beam(s) interacts with the particles in the sample by diffraction, refraction, reflection, scattering, and absorption with re-emission at various different wavelengths depending on the characteristics of the particle such as its size, internal structure, and the presence of one or more fluorescent molecules attached to or naturally present on or in the particle. The fluorescence emissions as well as the diffracted light, refracted light, reflected light, and scattered light may be routed to one or more of the forward scatter detector 130, the side scatter detector 135, and the one or more fluorescent emission detectors 160a-f through one or more of the beam splitters 145a-g, the bandpass filters 150a-e, the longpass filters 155a-b, and the fluorescence collection lens 140.

The fluorescence collection lens 140 collects light emitted from the particle-laser beam interaction and routes that light towards one or more beam splitters and filters. Bandpass filters, such as bandpass filters 150a-e, allow a narrow range of wavelengths to pass through the filter. For example, bandpass filter 150a is a 510/20 filter. The first number represents the center of a spectral band. The second number provides a range of the spectral band. Thus, a 510/20 filter extends 10 nm on each side of the center of the spectral band, or from 500 nm to 520 nm. Shortpass filters transmit wavelengths of light equal to or shorter than a specified wavelength. Longpass filters, such as longpass filters 155a-b, transmit wavelengths of light equal to or longer than a specified wavelength of light. For example, longpass filter 155a, which is a 670 nm longpass filter, transmits light equal to or longer than 670 nm. Filters are often selected to optimize the specificity of a detector for a particular fluorescent dye. The filters can be configured so that the spectral band of light transmitted to the detector is close to the emission peak of a fluorescent dye.

Beam splitters direct light of different wavelengths in different directions. Beam splitters can be characterized by filter properties such as shortpass and longpass. For example, beam splitter 145g is a 620 SP beam splitter, meaning that the beam splitter 145g transmits wavelengths of light that are 620 nm or shorter and reflects wavelengths of light that are longer than 620 nm in a different direction. In one embodiment, the beam splitters 145a-g can comprise optical mirrors, such as dichroic mirrors.

The forward scatter detector 130 is positioned slightly off axis from the direct beam through the flow cell and is configured to detect diffracted light, the excitation light that travels through or around the particle in mostly a forward direction. The intensity of the light detected by the forward scatter detector is dependent on the overall size of the particle. The forward scatter detector can include a photodiode. The side scatter detector 135 is configured to detect refracted and reflected light from the surfaces and internal structures of the particle, and tends to increase with increasing particle complexity of structure. The fluorescence emissions from fluorescent molecules associated with the particle can be detected by the one or more fluorescent emission detectors 160a-f. The side scatter detector 135 and fluorescent emission detectors can include photomultiplier tubes. The signals detected at the forward scatter detector 130, the side scatter detector 135 and the fluorescent emission detectors can be converted to electronic signals (voltages) by the detectors. This data can provide information about the sample.

One of skill in the art will recognize that a flow cytometer in accordance with an embodiment of the present invention is not limited to the flow cytometer depicted in FIG. 1, but can include any flow cytometer known in the art. For example, a flow cytometer may have any number of lasers, beam splitters, filters, and detectors at various wavelengths and in various different configurations.

In operation, cytometer operation is controlled by a controller/processor 190, and the measurement data from the detectors can be stored in the memory 195 and processed by the controller/processor 190. Although not shown explicitly, the controller/processor 190 is coupled to the detectors to receive the output signals therefrom, and may also be coupled to electrical and electromechanical components of the flow cytometer 100 to control the lasers, fluid flow parameters, and the like. Input/output (I/O) capabilities 197 may be provided also in the system. The memory 195, controller/processor 190, and I/O 197 may be entirely provided as an integral part of the flow cytometer 110. In such an embodiment, a display may also form part of the I/O capabilities 197 for presenting experimental data to users of the cytometer 100. Alternatively, some or all of the memory 195 and controller/processor 190 and I/O capabilities may be part of one or more external devices such as a general purpose computer. In some embodiments, some or all of the memory 195 and controller/processor 190 can be in wireless or wired communication with the cytometer 110. The controller/processor 190 in conjunction with the memory 195 and the I/O 197 can be configured to perform various functions related to the preparation and analysis of a flow cytometer experiment.

The system of FIG. 1 includes six different detectors that detect fluorescent light in six different wavelength bands (which may be referred to herein as a "filter window" or "fluorescence channel" for a given detector) as defined by the configuration of filters and/or splitters in the beam path from the flow cell 125 to each detector. Different fluorescent molecules used for a flow cytometer experiment will emit light in their own characteristic wavelength bands. The particular fluorescent labels used for an experiment and their associated fluorescent emission bands may be selected to generally coincide with the filter windows of the detectors. However, as more detectors are provided, and more labels are utilized, perfect correspondence between filter windows and fluorescent emission spectra is not possible. It is generally true that although the peak of the emission spectra of a particular fluorescent molecule may lie within the filter window of one particular detector, some of the emission spectra of that label will also overlap the filter windows of one or more other detectors. This may be referred to as spillover.

The I/O 197 can be configured to receive data regarding a flow cytometer experiment having a panel of fluorescent labels and a plurality of cell populations having a plurality of markers, each cell population having a subset of the plurality of markers. The I/O 197 can also be configured to receive biological data assigning one or more markers to one or more cell populations, marker density data, emission spectrum data, data assigning labels to one or more markers, and cytometer configuration data. Flow cytometer experiment data, such as label spectral characteristics and flow cytometer configuration data can also be stored in the memory 195. The controller/processor 190 can be configured to evaluate one or more assignments of labels to markers.

Figure 2:
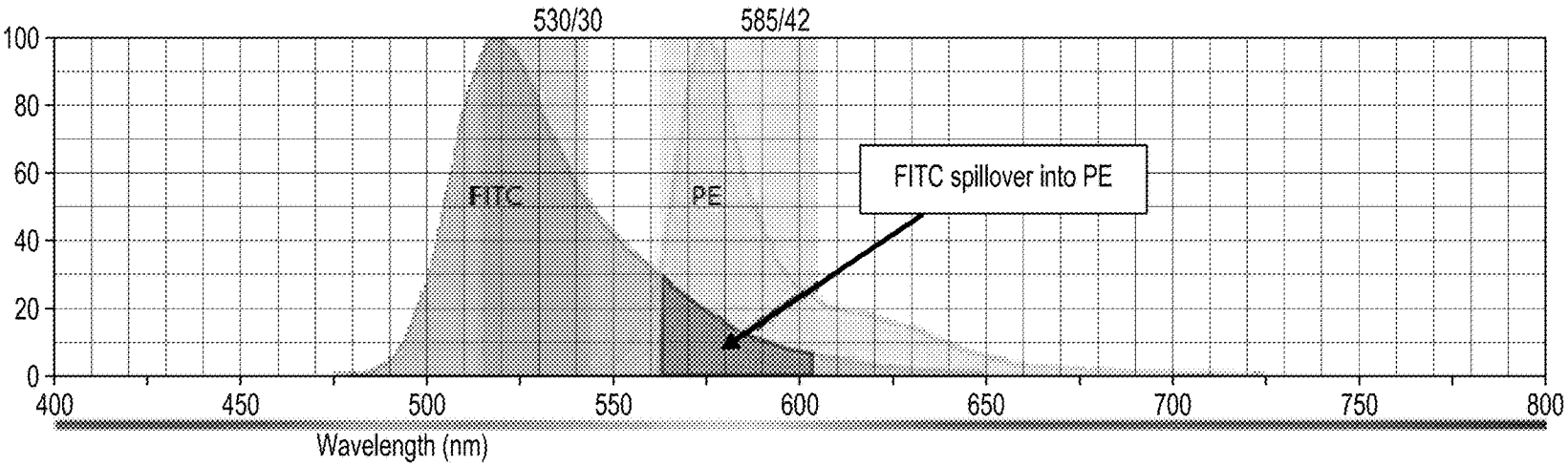
FIG. 2 depicts a graph showing examples of the emission spectra of labels and the filter windows of photodetectors in accordance with the present invention.

FIG. 2 shows an illustrative example of spillover caused by overlapping emissions spectra for different labels. FIG. 2 shows the emission spectra of markers labeled with FITC, represented by the curve extending from a wavelength of approximately 475 nm to 650 nm, and the filter window for a "FITC detector." One or more filters, such as bandpass filter 150b as depicted in FIG. 1, can be placed in front of the detector, limiting the range of wavelengths that can reach the detector, the range of wavelengths constituting a filter window. The filter window for the FITC detector is 530/30, meaning that the filter window extends from 515 nm to 545 nm. The FITC filter window is represented by the shaded rectangle extending from 515 nm to 545 nm. FIG. 2 also shows the emission spectra of markers labeled with PE, represented by the curve extending from approximately 525 nm to approximately 725 nm. One or more filters, such as bandpass filter 150c as depicted in FIG. 1, can be placed in front of the detector. The filter window for the PE detector is 585/42, meaning that the filter window extends from 564 nm to 606 nm. The PE filter window is represented by the shaded rectangle extending from 564 nm to 606 nm. FIG. 2 illustrates that a portion of the emissions spectra for FITC overlaps the filter window for the PE detector, labeled as "FITC spillover into PE." Therefore, some of the fluorescence emission of the FITC label is detected in the PE detector and measured along with the fluorescence emission of the PE label. Spillover can cause inaccurate conclusions to be drawn regarding the abundance of labels present on a particle. This problem can be especially acute for recent uses of flow cytometers as more labels and detectors are utilized, which reduces the separation of fluorescent peaks and filter windows. Given also the increasing number of fluorescent labels available (generally dozens of options are available to an experimenter), with a variety of peak wavelengths, emission intensities and energies, and spectral width characteristics, the variety of marker densities on cells being characterized, as well as in some cases selectable filter windows, it is very challenging to design a suitable set up for a flow cytometer experiment. A further complication is the autofluorescence of cells or other particles being characterized. This autofluorescence signal will also overlap one or more filter windows causing noise in the measurements. The autofluorescence noise signal can further be dependent on the type of particle/cell being interrogated.

The signal captured at a fluorescent emission detector can comprise contributions from one or more fluorescent labels, a system background signal, and the autofluorescence noise signal. The system background, often referred to as "baseline," can be removed from a measured signal through a baseline restore process, wherein a baseline signal can be estimated from time intervals in a cytometry experiment in which no event is occurring and then subtracted from the measured signal. To compensate for autofluorescence, in conventional compensation techniques, a "negative" or unstained sample, and a "positive" sample, one containing cells stained with a single dye, can be measured for each fluorescent dye to be used in a cytometry experiment. A single global negative population can be defined from an unstained sample for each dye. The median fluorescence intensity (MFI) of the single global negative population can be treated as the autofluorescence noise signal of the sample and can be subtracted from data of the positive sample to calculate an autofluorescence spillover value. However, when a marker of interest expresses on more than one cell type in a sample, the conventional method may fail to accurately remove the autofluorescence noise signal because the autofluorescence noise signal of each cell type can vary in strength. Consequently, autofluorescence can be mischaracterized as the fluorescence emission of one or more markers, even in the absence of such markers on a given cell type. This mischaracterization can make it difficult to distinguish populations not expressing a particular marker and those having a weak expression of that marker.

In accordance with embodiments described herein, autofluorescence noise signal estimation can be adapted to cell scatter characteristics. Cells with a similar size and complexity are more likely to have similar autofluorescence. Because size and complexity of a particle can be correlated to the intensity measured by forward scatter detectors and side scatter detectors, respectively, estimating an autofluorescence noise signal for a small area of a forward scatter-side scatter plot can lead to a more accurate value than estimating the autofluorescence noise signal based on a single median fluorescence intensity. Forward scatter and side scatter intensity measurements can be used in conjunction with associated fluorescence intensity values to provide a plurality of estimated autofluorescence noise signals, each signal associated with an area of a forward scatter-side scatter plot. The estimated autofluorescence noise signal values can then be subtracted from the signals captured by the fluorescent emission detectors for a corresponding stained sample based at least in part on the areas of the forward scatter-side scatter plot associated with the autofluorescence noise signals so that the measured data will more directly correlate to markers and labels of interest.

Figure 3:
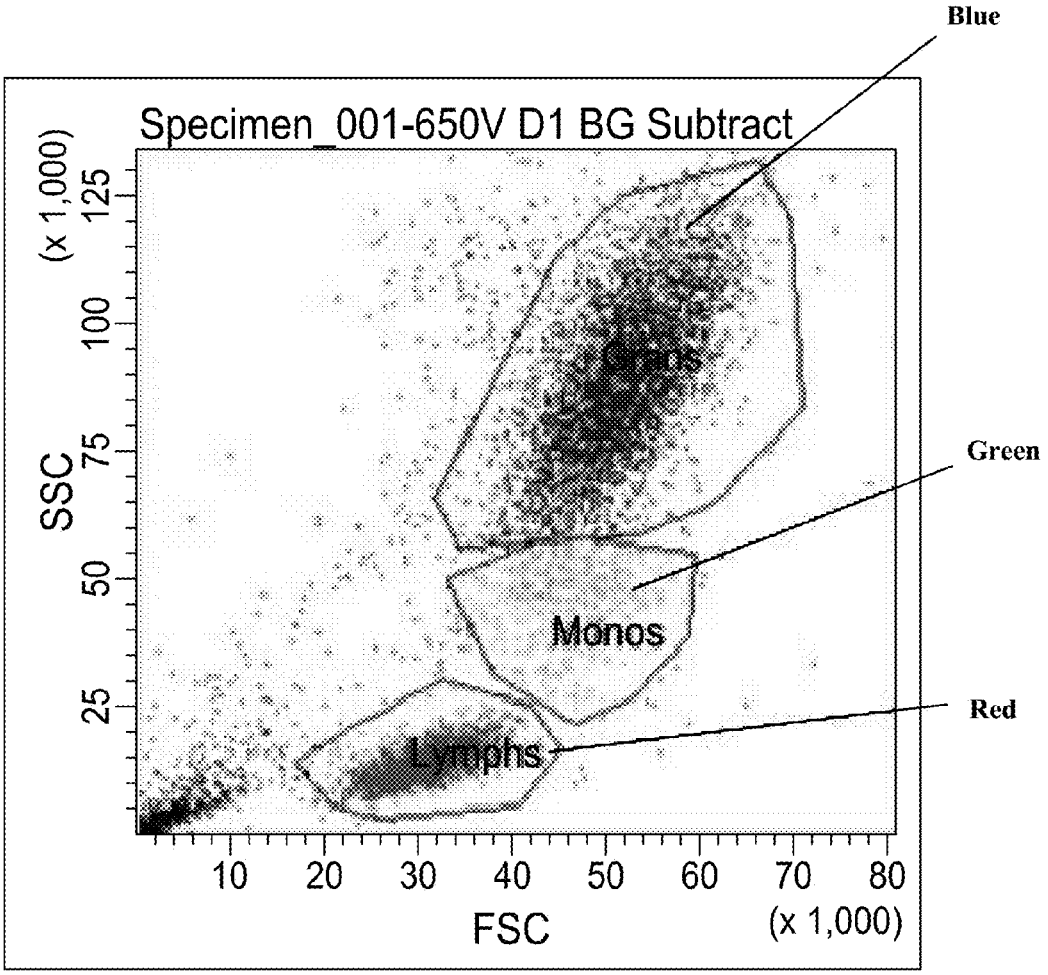
FIG. 3 depicts an example of a 2-D forward scatter-side scatter dot plot showing forward scatter and side scatter intensities for several cell populations in accordance with the present invention.

FIG. 3 shows an illustrative example of a 2-D forward scatter-side scatter dot plot. Correlated measurements of forward scatter intensity and side scatter intensity can allow for differentiation of cell types in a heterogeneous cell population. Each event in a flow cytometer experiment has a position in the forward scatter-side scatter plot based on the values measured by the forward scatter and side scatter detectors. Therefore, each dot shown in FIG. 3 is representative of the forward scatter and side scatter measurements of one or more events. Cells of the same type are likely to have similar forward scatter and side scatter measurements, meaning that clusters of data points on a 2-D forward scatter-side scatter plot may be representative of a single cell population. FIG. 3 shows a forward scatter-side scatter dot plot for an unstained sample containing a plurality of cell populations, lymphocytes, monocytes, and granulocytes, measured using a flow cytometer. The data points representing lymphocyte measurements are depicted in red. The data points representing monocyte measurements are depicted in green. The data points representing granulocyte measurements are depicted in blue. The data points representing lymphocyte measurements are labeled "Lymphs". The data points representing monocyte measurements are labeled "Monos". The data points representing granulocyte measurements are labeled "Grans". The colors, as well as the gates drawn around each population, are shown for illustrative purposes only.

Figure 4:
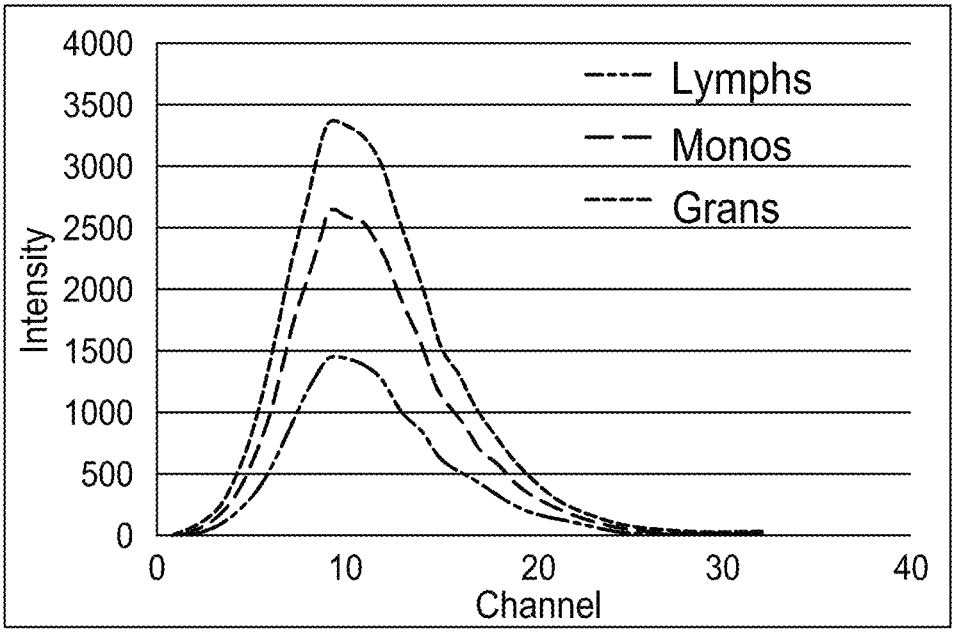
FIG. 4 depicts an example of a histogram displaying the averaged autofluorescence spectra of several cell populations in accordance with the present invention.

FIG. 4 shows an illustrative example of a histogram displaying the averaged autofluorescence spectra of lymphocytes, monocytes, and granulocytes measured from an unstained sample in the 400-800 nm range using a flow cytometer. As depicted in FIG. 4, the autofluorescence intensity values are different for each cell population, and the difference varies across fluorescence channels. As described above, forward scatter and side scatter intensity measurements for an unstained sample containing a plurality of cell types, such as the measurements shown for the lymphocytes, monocytes, and granulocytes in FIG. 3, can be used in conjunction with associated fluorescence intensity values, such as those depicted in FIG. 4, to provide a plurality of estimated autofluorescence noise signals, each signal associated with a region of a forward scatter-side scatter plot.

Figure 5:
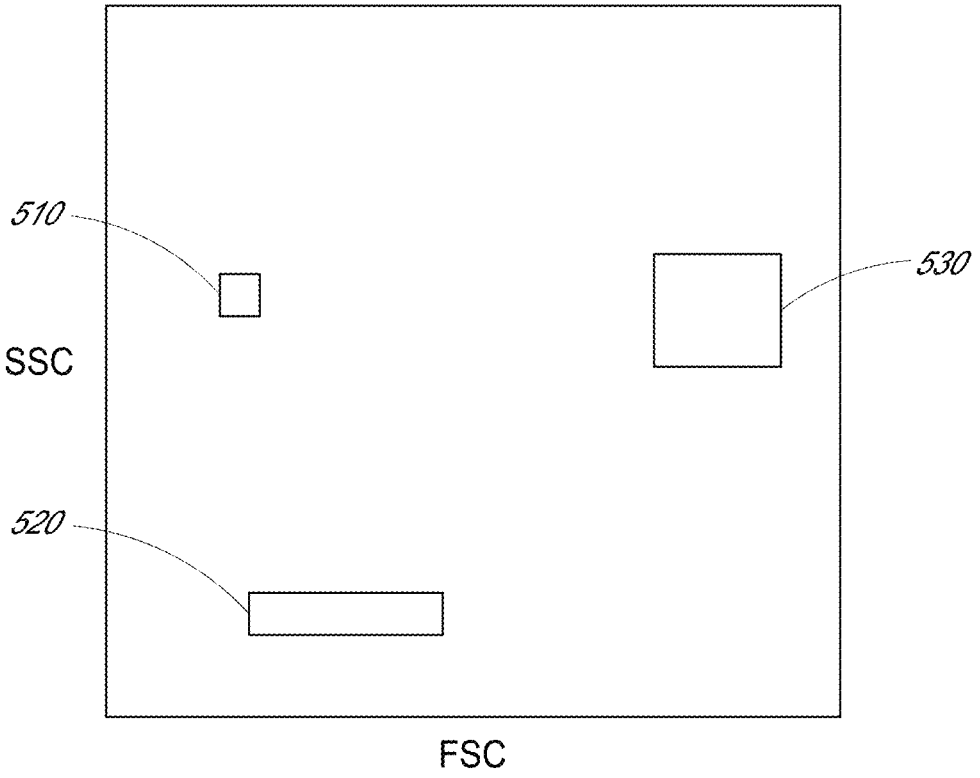
FIG. 5 depicts an example of several plot regions in accordance with the present invention.

The forward scatter-side scatter plot regions can correlate to one or more autofluorescence intensity values based at least in part on the measurements for the events of the unstained sample. In one embodiment, the forward scatter-side scatter plot regions can include a set of non-overlapping ranges of forward scatter intensity values and side scatter intensity values. The autofluorescence intensity value associated with a plot region can include a median or an average of the measured intensity associated with events of the unstained sample located in the plot region. FIG. 5 shows an illustrative example of several plot regions: region 510, region 520, and region 530. Each plot region can be associated with an autofluorescence intensity value for each fluorescence channel. For example, running an unstained sample through the flow cytometer depicted in FIG. 1 can result in six autofluorescence intensity values associated with each plot region, one for the each of the six fluorescent emission detectors. For fluorescent emission detector 160a of FIG. 1, corresponding to a fluorescence channel FL1, there is an autofluorescence intensity value $\delta_1$ associated with plot region 510, an autofluorescence intensity value $\alpha_1$ associated with plot region 520, and an autofluorescence intensity value $\beta_1$ associated with plot region 530. For fluorescent emission detector 160b of FIG. 1, corresponding to a fluorescence channel FL2, there is an autofluorescence intensity value $\delta_2$ associated with plot region 510, an autofluorescence intensity value $\alpha_2$ associated with plot region 520, and an autofluorescence intensity value $\beta_2$ associated with plot region 530. Fluorescent emission detectors 160c-f can each have an autofluorescence intensity value associated with each plot region as well. In some embodiments, the plot regions can be square in shape. The dimensions of the plot regions may be selected based at least in part on the density of events at different locations in the forward scatter-side scatter plot of events. Accordingly, plot regions for a single unstained sample may be of several different sizes. For example, a plot region at a location with a high density of events may be smaller than a plot region at a location with a relatively low density of events.

Figure 6A:
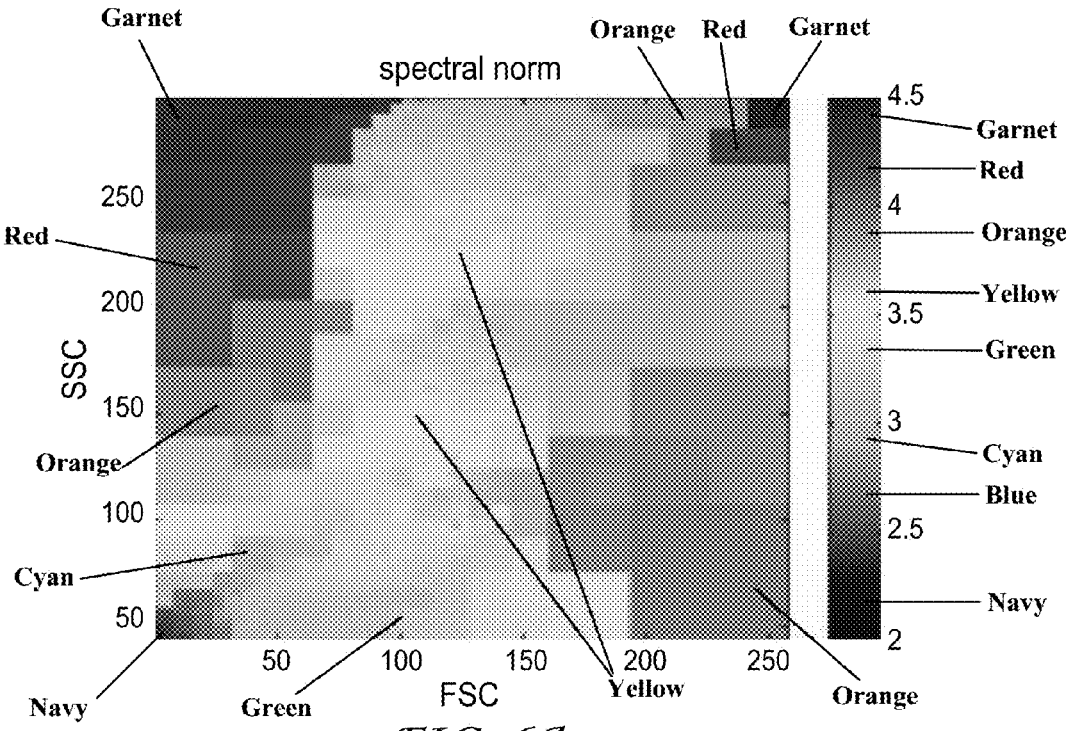
FIG. 6A depicts an example of an autofluorescence intensity map in accordance with the present invention.
Figure 6B:
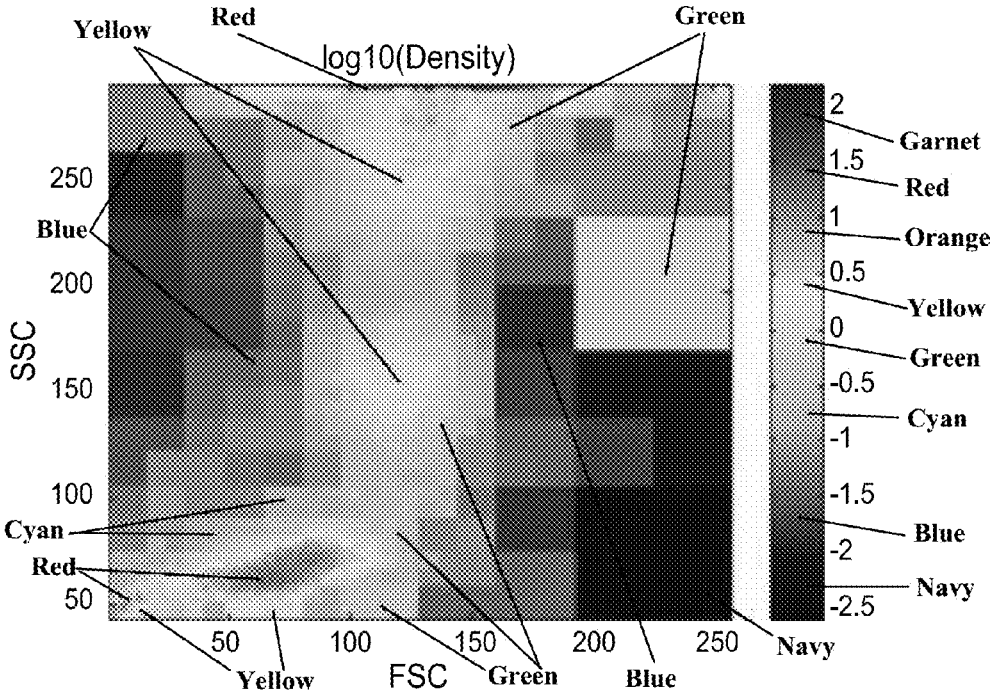
FIG. 6B depicts an example of an event density map in accordance with the present invention.

In one embodiment, the fluorescence intensity values measured for an unstained sample are associated with the forward scatter and side scatter intensity measurements through an autofluorescence intensity map. An illustrative example of an event density map is shown in FIG. 6B. FIG. 6A shows the autofluorescence intensity map derived from the events of FIG. 6B. An autofluorescence intensity map shows the measured fluorescence intensity at a fluorescence channel for given forward scatter and side scatter intensities. The map can configured so that each forward scatter-side scatter location is associated with a plot region. Each plot region can correlate to the median or average autofluorescence intensity from the events in that region.

The median or average autofluorescence intensity values measured for an unstained sample in a selected region of an FSC-SSC plot can be subtracted from fluorescence intensity measurements for a stained sample that are in the same selected region of the FSC-SSC plot to compensate for the autofluorescence noise signal on the measured data. For every event measured for a stained sample, the forward scatter-side scatter location of the event can be correlated to a forward scatter-side scatter region for the unstained sample, and an autofluorescence intensity value can then be found for that region, for example, by using an autofluorescence intensity map such as the map illustrated in FIG. 6A which may be stored as a look up table or other data format. The autofluorescence intensity value at the corresponding forward scatter-side scatter region can then be subtracted from the measured intensity of the stained sample at the associated plot location. For example, with reference to FIG. 5, if an event is measured for a stained sample and the forward scatter-side scatter location of the event correlates to plot region 510, the effect of the autofluorescence noise signal on the measured data can be compensated for by subtracting the autofluorescence intensity value associated with that region for each detector from the measured intensity value measured for the stained sample at each detector respectively. Thus, autofluorescence intensity value $\delta_1$ can be subtracted from a measured intensity value for the event at fluorescent emission detector 160a and autofluorescence intensity value $\delta_2$ can be subtracted from a measured intensity value for the event at fluorescent emission detector 160b. The measured intensity values for the event at fluorescent emission detectors 160c-f can also be subtracted from the autofluorescence intensity values associated with region 510 for those detectors.

Figures 7A, 7B, 7C:
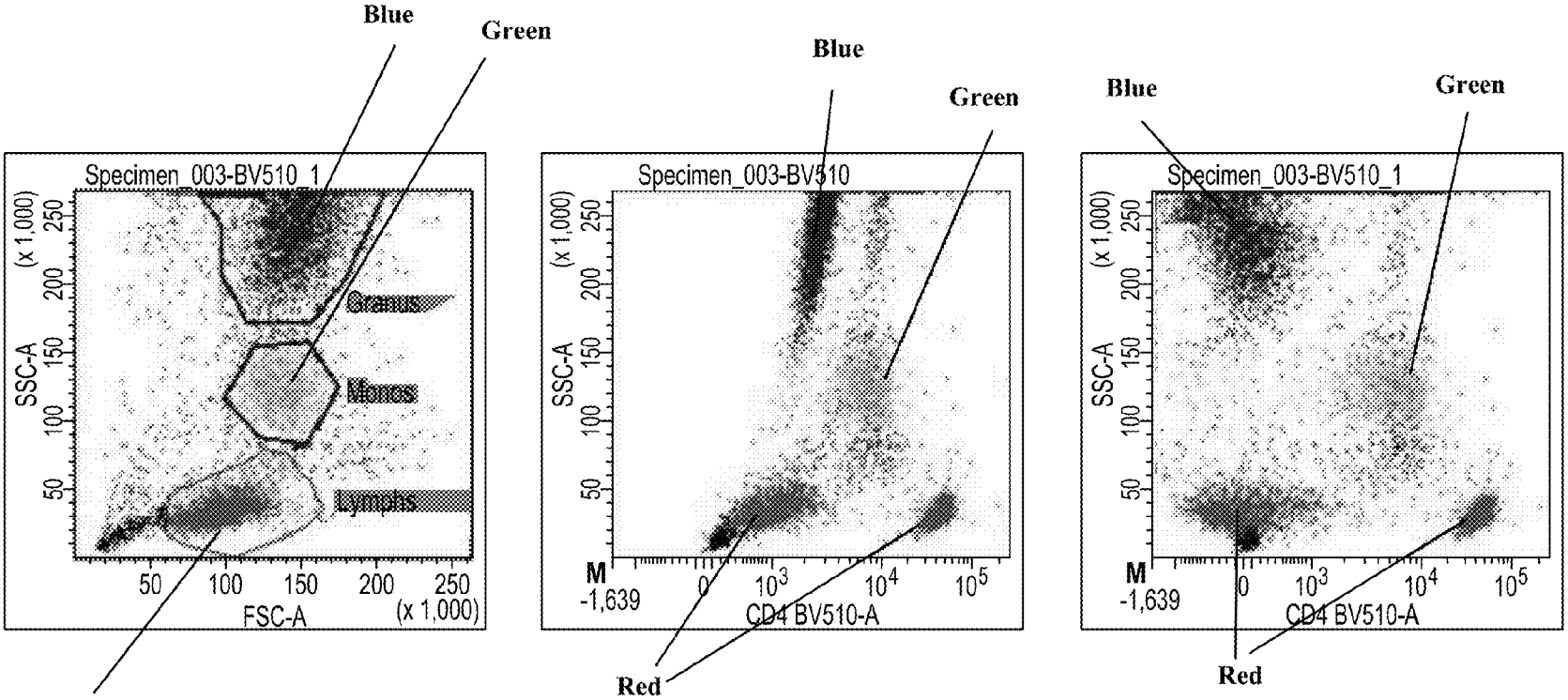
FIG. 7A depicts an example of a forward scatter-side scatter plot of a stained sample in accordance with the present invention.
FIG. 7B depicts an example of a dot plot showing the side scatter intensity and the measured fluorescence intensity of a label for the stained sample of FIG. 6A.
FIG. 7C depicts an example of a dot plot showing the data of FIG. 6B after removing autofluorescence noise signals in accordance with the present invention.

FIGS. 7A-C show an illustrative example of a set of dot plots processed in accordance with the above principles. FIG. 7A depicts a forward scatter-side scatter plot of a sample stained with BV510, a fluorescent dye which can be used as a label for CD4 markers. The data points in the sample are shown gated and in color for illustrative purposes, with lymphocytes shown in red, monocytes shown in green, and granulocytes shown in blue. The lymphocytes, monocytes, and granulocytes are labeled "Lymphs", "Monos", and "Granus," respectively, in FIG. 7A. FIG. 7B shows a dot plot depicting the side scatter intensity and the measured fluorescence intensity of BV510 for the sample of FIG. 7A using conventional data analysis. As illustrated by FIG. 7B, there are measured intensity values for the lymphocyte, monocyte, and granulocyte populations, implying that CD4 is expressed on each of those populations. FIG. 7C shows a dot plot depicting the data of FIG. 7B after removing the autofluorescence noise signals in accordance with the present invention. After removal, non-expressing cells should have median fluorescence intensity values close to zero. FIG. 7C shows two groups of lymphocytes, a first group having measured intensity values close to zero and a second group of lymphocytes with measured intensity values between $10^4$ and $10^5$. Most of the granulocytes also have measured intensity values close to zero. Consequently, it can be concluded that the lymphocytes of the first group and most of the granulocytes do not express CD4.

Figure 8:
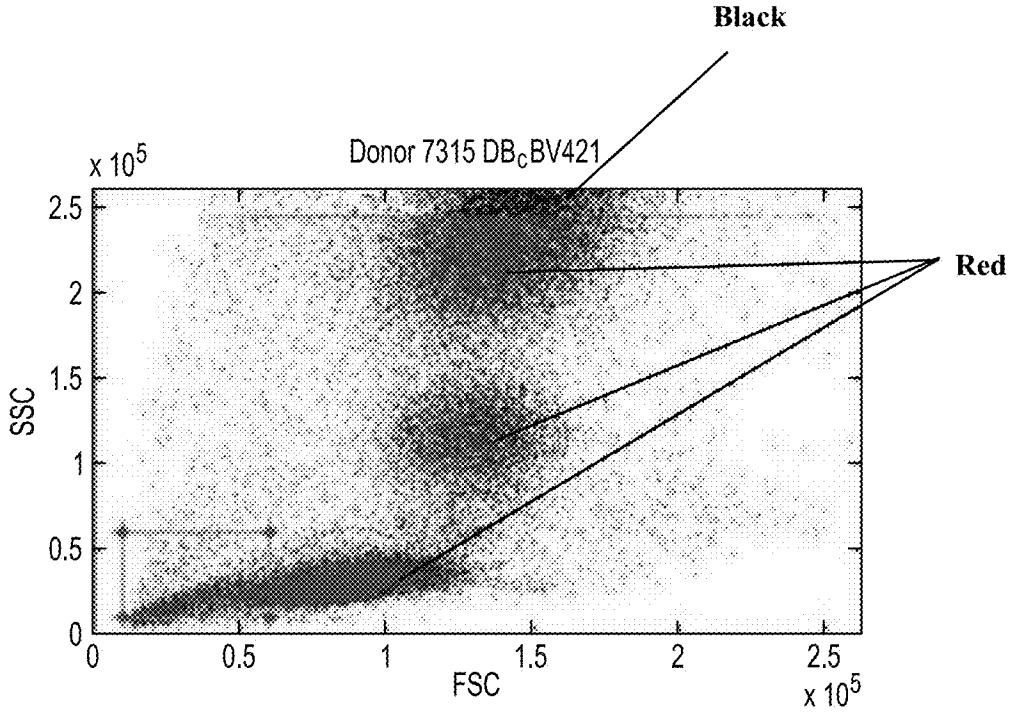
FIG. 8 depicts an example of a forward scatter-side scatter dot plot for an unstained sample scaled to overlay a forward scatter-side scatter dot plot for a stained sample in accordance with the present invention.

When assembling the autofluorescence intensities for the unstained FSC-SSC regions, scatter gain difference between the measurements of stained and unstained samples can lead to different FSC-SSC event locations for the same cell types between stained and unstained experiments. This may cause incorrect correlations between the forward scatter-side scatter locations of one or more events of the stained sample and the forward scatter-side scatter regions of the unstained sample. In some embodiments, the forward scatter-side scatter plot locations of the events measured in the unstained sample can be adjusted based at least in part on a comparison between the events measured for the unstained sample and the events measured for the stained sample. The scale of the forward scatter-side scatter measurements for an unstained sample may be adjusted so that the scatter density pattern better matches that of the stained sample. An illustrative example of such an adjustment is depicted in FIG. 8. FIG. 8 shows the overlay of a fitted unstained forward scatter-side scatter plot in red to the forward scatter-side scatter plot of a stained sample, shown in black. Such an adjustment can be performed, for example, by applying a scaling factor to the unstained sample data.

In one embodiment, determining a scaling factor includes converting the forward scatter-side scatter plots of both the unstained and stained sample to grayscale images based on density. Morphological image opening can then be performed to remove the small objects, i.e., the scattered dots. The resulting images can then be thresholded to create binary images. One or more of the largest connected regions can then be determined for each image, and centroids for the one or more regions can be calculated. A scaling factor can then be calculated using the ratio of the centroid positions in each dimension of the unstained image to the stained image.

The forward scatter-side scatter data can then be adjusted using the determined scaling factor.

Figure 9:
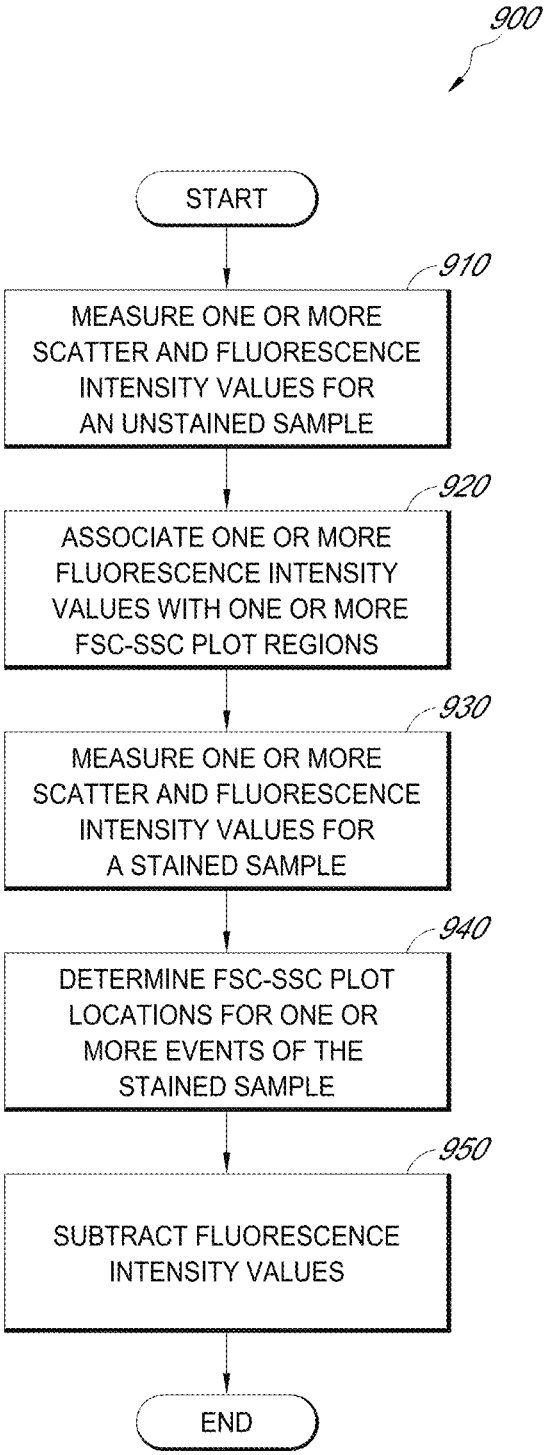
FIG. 9 depicts a flowchart of a process for operating a flow cytometer in accordance with an illustrative embodiment of the present invention.

FIG. 9 shows a flowchart of one embodiment of a process 900 of operating a flow cytometer in accordance with an embodiment of the present invention. The process 900 begins at a step 910, wherein one or more forward scatter values, one or more side scatter values, and one or more fluorescence intensity values are measured for one or more events of an unstained sample using a flow cytometer, such as flow cytometer 110 as depicted in FIG. 1. The one or more forward scatter values, one or more side scatter values, and one or more fluorescence intensity values can be measured by one or more detectors such as forward scatter detector 130, side scatter detector 135, and fluorescent emission detectors 160a-f.

After the forward scatter, side scatter, and fluorescence intensity values are measured for the events of the unstained sample, the process 900 moves to a step 920, wherein one or more fluorescence intensity values are associated with one or more forward scatter-side scatter plot regions based at least in part on the measurements taken for the unstained sample. The fluorescence intensity values can be associated with the forward scatter-side scatter plot regions by a processing circuit, such as controller/processor 190 as depicted in FIG. 1. FIG. 3 depicts an example of a forward scatter-side scatter plot in accordance with an embodiment of the present invention. The fluorescence intensity values can be associated with the one or more forward scatter-side scatter plot regions in an autofluorescence intensity map, such as the autofluorescence intensity map depicted in FIGS. 6A. Alternatively, the associated data can be stored without generating an autofluorescence intensity map.

After the fluorescence intensity values are associated with the forward scatter-side scatter plot regions, the process 900 moves to a step 930, wherein one or more forward scatter values, one or more side scatter values, and one or more fluorescence intensity values are measured for one or more events of a stained sample using the flow cytometer. The stained sample can be stained with a single fluorescent dye and may be from the same donor as the unstained sample.

After the forward scatter, side scatter, and fluorescence intensity values are measured for the events of the stained sample, the process 900 moves to a step 940, wherein forward scatter-side scatter plot locations are determined for the one or more events of the stained sample by the processor.

After the forward scatter-side scatter plot locations are determined, the process 900 moves to a step 950, wherein, for each of the events of the stained sample, the fluorescence intensity value of the unstained sample associated with the forward scatter-side scatter plot region that contains the forward scatter-side scatter plot location of the stained sample event is subtracted from the measured fluorescence intensity value of the stained sample associated with that forward scatter-side scatter plot location.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as general purposes computers, wireless communication devices, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A method for operating a flow cytometer having a forward scatter detector, a side scatter detector, and a plurality of fluorescent emission detectors, each fluorescent emission detector corresponding to a fluorescence channel, comprising:

measuring one or more forward scatter values at the forward scatter detector, one or more side scatter values at the side scatter detector, and one or more fluorescence intensity values at one or more of the plurality of fluorescent emission detectors for one or more events of a first [plurality of cell populations] *cell population* of an unstained sample of a subject using the flow cytometer;

generating a mean *or median* fluorescence intensity value for [each] *a* forward scatter-side scatter plot region [of a plurality of forward scatter-side scatter plot regions] for one or more of the plurality of fluorescent emission detectors based at least in part on measurements of the one or more forward scatter values, one or more side scatter values[,] and one or more fluorescence intensity values for the one or more events of the first [plurality of cell populations] *cell population* of the unstained sample;

measuring one or more forward scatter values, one or more side scatter values, and one or more fluorescence intensity values at one or more of the plurality of fluorescent emission detectors for one or more events of a second [plurality of cell populations] *cell population* of a stained sample of the subject using the flow cytometer;

determining forward scatter-side scatter plot locations for the one or more events of the second [plurality of cell populations] *cell population* of the stained sample; and for [each of the] one or more events of the second [plurality of cell populations] *cell population* of the stained sample, subtracting a mean *or median* fluorescence intensity value associated with the forward scatter-side scatter plot region that contains the forward scatter-side scatter plot location of the [event] *one or more events* of the second [plurality of cell populations] *cell population* of the stained sample for at least one of the plurality of fluorescent emission detectors from a measured fluorescence intensity value of the event of the second [plurality of cell populations] *cell population* of the stained sample at that forward scatter-side scatter plot location measured at the at least one of the plurality of fluorescent emission detectors.

2. The method of claim 1, further comprising adjusting forward scatter-side scatter plot locations of the events measured for the unstained sample based at least in part on a comparison between the events measured for the unstained sample and the events measured for the stained sample.

3. The method of claim 2, wherein the adjusting comprises adjusting a scale of the forward scatter-side scatter plot for the events of the unstained sample to more closely match event locations of the unstained sample to event locations of the stained sample.

4. The method of claim 1, wherein forward scatter-side scatter plot regions are defined as a set of non-overlapping ranges of forward scatter intensity values and side scatter intensity values.

5. The method of claim 4, wherein the regions are square.

6. The method of claim 4, wherein the dimensions of the regions are selected based at least in part on the density of events at different locations in the forward scatter-side scatter plot of events.

7. The method of claim 1, wherein measuring one or more fluorescence intensity values for one or more events of an unstained sample is performed at a plurality of the fluorescent emission detectors, wherein measuring one or more fluorescence intensity values for one or more events of a stained sample is performed at the same plurality of fluorescent emission detectors used to measure the one or more fluorescence intensity values for the unstained sample.

8. The method of claim 7, comprising, for each of the one or more events of the stained sample, subtracting a plurality of fluorescence intensity values associated with the forward scatter-side scatter plot region that contains the forward scatter-side scatter plot location of the stained sample event for the plurality of fluorescent emission detectors, from a plurality of measured fluorescence intensity values of the stained sample event at that forward scatter-side scatter plot location measured at the plurality of fluorescent emission detectors, wherein each fluorescence intensity value associated with the forward scatter-side scatter plot region that contains that forward scatter-side scatter plot location of the stained sample event subtracted from a measured fluorescence intensity value of the stained sample is associated with the same fluorescent emission detector as the measured fluorescence intensity value of the stained sample.

9. The method of claim 1, wherein the unstained sample and the stained sample comprise a plurality of cell types.

10. A flow cytometer, comprising:

an excitation laser;

a fluidics system configured to transport particles from one or more samples into a beam path of the excitation laser;

one or more detectors, wherein the detectors are configured to:

measure one or more forward scatter values, one or more side scatter values, and one or more fluorescence intensity values for one or more events of a first [plurality of cell populations] *cell population* of an unstained sample of a subject; and measure one or more forward scatter values, one or more side scatter values, and one or more fluorescence intensity values for one or more events of a second [plurality of cell populations] *cell population* of a stained sample of the subject; and a processing circuit, wherein the processing circuit is configured to:

generate a mean *or median* fluorescence intensity value for [each] *a* forward scatter-side scatter plot region [of a plurality of forward scatter-side scatter plot regions] based at least in part on measurements of the one or more forward scatter values, one or more side scatter values, and one or more fluorescence intensity values for the one or more events of the first [plurality of cell populations] *cell population* of the unstained sample;

determine forward scatter-side scatter plot locations for the one or more events of the second [plurality of cell populations] *cell population* of the stained sample; and for [each of the] one or more events of the second [plurality of cell populations] *cell population* of the stained sample, subtract a mean *or median* fluorescence intensity value associated with the forward scatter-side scatter plot region that contains the forward scatter-side scatter plot location of the [event] *events* of the second [plurality of cell populations] *cell population* of the stained sample from a measured fluorescence intensity value of the event of the second [plurality of cell populations] *cell population* of the stained sample at that forward scatter-side scatter plot location.

11. The flow cytometer of claim 10, wherein the processing circuit is further configured to adjust forward scatter-side scatter plot locations of the events measured for the unstained sample based at least in part on a comparison between the events measured for the unstained sample and the events measured for the stained sample.

12. The flow cytometer of claim 11, wherein the processor is configured to adjust a scale of the forward scatter-side scatter plot for the events of the unstained sample to more closely match event locations of the unstained sample to event locations of the stained sample.

13. The flow cytometer of claim 11, wherein the unstained sample and the stained sample comprise a plurality of cell types.

14. The flow cytometer of claim 10, wherein the one or more detectors are configured to measure at one or more fluorescence channels.

15. The flow cytometer of claim 10, wherein the one or more detectors comprise a plurality of fluorescent emission detectors, wherein each detector is configured to measure a fluorescence intensity value for one or more events of an unstained sample, wherein each fluorescent emission detector is further configured to measure a fluorescence intensity value for one or more events of a stained sample.

16. The flow cytometer of claim 15, wherein for each of the one or more events of the stained sample, the processing circuit is configured to subtract fluorescence intensity values associated with the forward scatter-side scatter plot region that contains the forward scatter-side scatter plot location of the stained sample event for each of the plurality of fluorescent emission detector from measured fluorescence intensity value of the stained sample event at that forward scatter-side scatter plot location for each of the plurality of fluorescent emission detectors, wherein each fluorescence intensity value associated with the forward scatter-side scatter plot region that contains that forward scatter-side scatter plot location of the stained sample event subtracted from a measured fluorescence intensity value of the stained sample is associated with the same fluorescent emission detector as the measured fluorescence intensity value of the stained sample.

*17. The method of claim 1, wherein the method comprises generating a mean or median fluorescence intensity value for each forward scatter-side scatter plot region of a plurality of forward scatter-side scatter plot regions for one or more of the plurality of fluorescent emission detectors, wherein the fluorescence intensity value is an average or median of the measured fluorescence intensity associated with events of the unstained sample located within each respective forward scatter-side scatter plot region for the one of the plurality of fluorescent emission detectors.*

* * * * *